United States Patent [19]

Uzgiris et al.

[11] Patent Number: 4,668,584

[45] Date of Patent: May 26, 1987

[54] METHOD FOR FORMING 2-D CRYSTALS OF PROTEINS AND MACROMOLECULES

[75] Inventors: Egidijus E. Uzgiris; James R. Yates, both of Schenectady, N.Y.

[73] Assignee: General Electric Company, Schenectady, N.Y.

[21] Appl. No.: 812,569

[22] Filed: Dec. 23, 1985

[51] Int. Cl.$^4$ .......................... B32B 9/00; C07K 3/00
[52] U.S. Cl. .......................... 428/408; 427/2; 428/420; 428/478.2; 424/85; 530/344; 530/387; 530/389; 530/390; 530/391; 530/396; 530/404; 530/408; 530/412; 530/414; 530/415; 530/422; 530/423; 530/424; 530/427
[58] Field of Search .......................... 260/112 B, 112 R; 424/85; 428/408, 420, 478.2; 427/2; 530/344, 387, 389, 390, 391, 396, 404, 408, 412, 414, 415, 422, 423, 424, 427

[56] References Cited

U.S. PATENT DOCUMENTS 4,172,827 10/1979 Giaever .......................... 260/112 R
4,489,133 12/1984 Kornberg .......................... 260/112 R X

OTHER PUBLICATIONS

E. E. Uzgiris & R. D. Kornberg, "Two-Dimensional Crystallization Technique for Imaging Macromolecules, with Application to Antigen-Antibody-Complement Complexes", *Nature*, vol. 301, Jan. 13, 1983, pp. 125–129.

*Primary Examiner*—Howard E. Schain
*Attorney, Agent, or Firm*—William A. Teoli; James C. Davis, Jr.; James Magee, Jr.

[57] ABSTRACT

A method is provided for forming ordered macromolecular protein arrays by avoiding a binding pathway that leads to densely packed, disordered states during protein crystal growth, by a diffusion limited process or by allowing controlled growth to occur by removal of the initial supported protein layer to a different environment.

5 Claims, No Drawings

METHOD FOR FORMING 2-D CRYSTALS OF PROTEINS AND MACROMOLECULES

BACKGROUND OF THE INVENTION

Prior to the present invention, as shown by Uzgiris et al., Two-Dimensional Crystallization Technique for Imaging Macromolecules with Application to Antigen-Antibody-Complement Complexes, Nature, Vol. 301, January 1983, pp. 125-129, techniques were available for growing protein arrays on lipid monolayers. Although the procedures described by Uzgiris et al. resulted in the production of ordered arrays of molecules as determined by optical defraction and by image processing of electron micrographs, the resulting ordered arrays were of small size and comprised a low portion of the total surface area as observed under an electron microscope. New techniques are therefore constantly being sought to improve the procedure for making ordered protein monolayers suitable for high resolution studies with electron microscopy as well as applications requiring ordered macromolecular films.

Experience has shown that conditions favoring two-dimensional crystallization of ordered monolayers require (1) fixation of molecules on a plane, (2) mobility of the molecules within the plane to allow sampling of various bonding arrangements, (3) identical orientation of all the molecules and (4) high concentration of molecules in the plane so that crystallization will be favored over two-dimensional liquid-like disorder. Depending upon the crystal nucleation rate for the bound protein, the surface of the lipid monolayer can quickly become saturated with bound protein yielding a highly dense and disordered condition referred to sometimes as the "protein jamming limit". It has been observed that once the jamming limit has been exceeded on the phospholipid monolayer, two-dimensional crystal growth rarely occurs.

The present invention is based on the discovery that significant improvements in crystallization of various proteins can be achieved by allowing the nucleation of the protein to occur on a phospholipid substrate by a slow diffusion limited process in a saline solution of the protein. Another procedure is allowing a monolayer of the protein to grow on the surface of a phospholipid film by conventional techniques as previously described above in Uzgiris et al. in Nature and thereafter transferring such coated phospholipid film to a different solution to promote the nucleation of the initial protein monolayer in the presence of the same protein at a lower concentration. A third procedure is transferring the coated phospholipid film to another solution having a different protein, or a salt solution, at a concentration different from the concentration of the protein in the original solution. In instances where a salt solution is used, a range of 0.15M to 0.6M is preferred particularly for promoting antibody crystal growth, and divalent ions such as calcium and magnesium have been found effective.

STATEMENT OF THE INVENTION

There is provided by the present invention, a method of promoting nucleation and crystal growth, while avoiding the jamming limit, of at least one macromolecular protein monolayer on a supported phospholipid film or a protein adsorbed on the surface of such phospholipid film comprising (1) effecting contact over a period of at least one hour between the supported phospholipid film and macromolecules of the protein in a diffusion limited process by floating the supported phospholipid film in a buffered saline solution injected with a drop of the protein in a nonhomogeneous manner, or having the buffered saline solution superimposed over a layer of the protein to provide a substantial build-up of ordered macromolecular arrays, (2) floating the phospholipid film in a buffered saline solution of the protein at a concentration of 10-200 micrograms/ml until a monolayer of the protein is formed, and (a) removing the coated phospholipid film and floating it in a solution of the same protein at a lower concentration, or (b) removing the coated phospholipid film and floating it in a solution of a different protein at a concentration of 10-100 micrograms/ml, or (c) removing the coated supported phospholipid film and floating it in a salt solution comprising an alkali metal salt having a concentration of at least 10 mM.

Lipids which can be utilized in the practice of the present invention are preferably phospholipids derived from either glycerol, which are more specifically phosphoglycerides having a glycerol backbone, two fatty acid chains, referred to sometimes as the "lipophilic region", and a phosphorylated alcohol, referred to sometimes as "hydrophilic region", or "polar head group". Additional phospholipids which can be used are phospholipids derived from sphingosine. In addition to phospholipids, glycolipids also can be utilized. Specific phospholipids which are preferred are, for example, N-dinitrophenylphosphatidylcaproylethanolamine, N-dinitrophenylaminocaproyl phosphatidylethanolamine, etc. Additional phospholipids, glycolipids and cholesterol lipids, which can be used in the practice of the invention, are further shown, for example, in Stryer, Biochemistry (Second Edition), pages 206-212, W. H. Freeman and Company, New York, 1981, and Ullman et al., U.S. Pat. No. 4,193,983, incorporated herein by reference.

Substrates which can be used in the practice of the present invention to support the lipid monolayer are for example nitrocellulose films, Formvar resin films, carbon coated film of such materials and thermoplastic film, such as Lexan ® polycarbonate, Noryl ® resin, Ultem ® polyetherimide, etc.

One method of making a supported lipid monolayer is by initially spreading a lipid monolayer on an air-water interface. A Teflon ® resin trough can be used to receive a few drops of the lipid which is generally provided in an organic solvent, such as hexane or cholorform. A substrate, for example, a silver grid used in electron microscope studies, can be coated with collodion (nitrocellulose) and thereafter carbon shadowed using a carbon-arc deposition procedure. The carbon treated substrate can be rendered hydrophilic by exposure to U.V. An effective UV treatment is exposure of a UV lamp (CANRAD HANOVIA, Cat. No. 7953-1) at a distance of 3 inches for 4 minutes at 20 mW/cm$^2$ under atmospheric conditions.

The resulting hydrophilic carbon coated grid can be passed through the lipid monolayer on the air-water interface in the Teflon ® resin trough to effect the deposition of the lipid monolayer on the hydrophilic carbon-coated silver grid surface. After withdrawal into air, the deposited lipid monolayer has its fatty-acid chains facing away from the surface of the grid and its polar head groups abutting the hydrophilic carbon coated silver grid.

The procedure can be repeated using the lipid monolayer carbon coated silver grid. The lipid monolayer coated silver grid can be passed through the air-water interface in the Teflon resin coated trough. A bilayer substrate composite is formed having a lipid bilayer with an interior lipophilic region and exterior hydrophilic regions. This procedure can be repeated several times if desired. In most instances, it is preferred not to exceed a bilayer.

The lipid polylayer-substrate composite can be allowed to dry or can be used directly prior to contact with macromolecules in an aqueous polar medium. Temperatures in the range of from about 0° C. to 70° C. can be employed during the incubation period. The conditions utilized in effecting the formation of the ordered macromolecular monolayer will vary widely depending upon the nature of the macromolecules. Accordingly, buffers such as 150 mM NaCl and 25 mM tris(hydroxymethyl)aminomethane (Tris), or 150 mM NaCl and 25 mM bis(2-hydroxyhydroxyethyl)imino tris(hydroxymethyl)methane can be used. It has been observed that the salt concentration can be readily varied from 50 mM to 400 mM NaCl and the buffer concentration from 0 to 75 mM without causing protein denaturation or protein aggregation. In pure salt solutions the desired pH is reached by addition of NaOH or HCl. Other common buffers which can be used are 150 mM NaCl with 25 mM [4-(2-hydroxyethyl)-1-piperazineethanesulfonic acid] (HEPES). The aforementioned buffers can be used as well as other ingredients to vary the ionic strength, viscosity and the like.

The concentration of the macromolecule in the aqueous media can vary widely and range from 1 microgram to several milligrams, per ml. of aqueous mixture.

Macromolecules which can be nucleated as ordered monolayers in the practice of the present invention are, for example, organic molecules having molecular weights of at least about 1,000 and up to about 1,000,000 or more. Macromolecules of particular interest are the polyamino acids as exemplified by polypeptides and proteins. There can be preferably employed antibodies such as IgG, IgM, IgA, IgE, enzymes and naturally occurring receptors such as avidin, cell surface receptors and histones. Another class of macromolecules which are of interest are polynucleotides or nucleic acids which can include DNA or RNA, where the DNA may be chromasomal, plasmid, viral and where the RNA can be messenger RNA, transfer RNA, ribosomal, synthetic, etc. In addition to being organic, the macromolecules also can include organometallics, such as organosilicon materials.

Polar solvents which can be used will generally not exceed 10 volume percent of the total aqueous polar solvent medium. Some of the polar solvents which can be used are, for example, alcohols such as methanol and ethanol, amides such as N,N-dimethylformamide, ketones for example acetone. In particular instances, polar solvents can be employed having only moderate water solubility.

Multiple monolayers of macromolecules can be bound in an ordered manner by using the monolayer incubated in accordance with the method of the present invention as a substrate. For example, the binding of a different antibody to an IgG ordered monolayer is based on the recognition of some exposed domain of the IgG antibody.

Separation of macromolecular arrays can be effected in particular instances by adjusting the pH of the incubating bath to achieve acidic conditions.

In order that those skilled in the art will be better able to practice the present invention, the following example is given by way of illustration and not by way of limitation.

EXAMPLE 1

Circular silver grids, obtained from the Ladd Research Company, having a diameter of 3 millimeters and a thickness of 40 microns were placed on a thin sheet of nitrocellulose that had been cast on a glass slide and then floated onto a water/air interface. The grids on the nitrocellulose sheet were then picked up onto a paper strip to produce a composite of several silver grids on paper covered with nitrocellulose. Nitrocellulose coated grids were then shadowed with vapor deposited carbon utilizing a carbon arc in a relatively clean high vacuum system. The carbon coated grids were then exposed for about 4 minutes under a UV lamp (CANRAD HANOVIA, Type "React") at a distance of 3 inches at about 20 mW/cm$^2$ in air. The UV treated carbon coated silver grids were then found to be hydrophilic as they wet readily upon being immersed in water.

A monolayer of N-dinitrophenylaminocaproylphosphatidylethanolamine was spread on an air/water interface in a Teflon ® resin trough. Hydrophilic carbon coated silver grids were then passed through the spread lipid monolayer. A composite of the silver grid and monolayer was formed with phospholipid heads abutting the hydrophilic carbon coated silver grid surface and the hydrocarbon chains exposed to the air. A second passage through the interface resulted in a deposition of a bilayer with polar head groups of the second layer facing away from the grid surface.

There was injected into the bottom of a well containing 20 microliters of a buffered saline solution of 150 mM of NaCl and 25 mM of tri(hydroxymethyl)methylamine (Tris), 1 microliter of IgG (monoclonal antidinitrophenyl) at 1 mg/ml. The pipet tip was slowly withdrawn and a silver grid as previously described, coated with a lipid bilayer, was floated on top of the solution. The diffusion time from the bottom of the well to the grid was estimated to be about 10 hours. There was obtained at a pH of 7 after a period of 20 hours at 18° C., large hexagonal, very highly ordered domains of crystalline IgG covering about 50% of the lipid surface.

In accordance with the above procedure, a bilayer was deposited onto a hydrophillic carbon coated grid by inserting the grid through the spread monolayer and then withdrawing into air again and then repeating the procedure once again. The coated grid was floated on a homogeneous solution of anti-DNP monoclonal IgG at 50 microliters in 150 mM NaCl and 50 mM Tris at pH 7 and incubated for about 20 hours at 18° C. There was obtained small hexagonal domains over only about 5% of the total lipid surface. An additional 15% of the area was composed of a low order linear phase and the remainder of the lipid surface was in a disordered liquid-like organization.

The above results show that the diffusion limited process of the present invention provides a superior opportunity for ordered crystal growth.

EXAMPLE 2

Phospholipid coated grids were incubated for 1 hour in 50 μg/ml IgE, anti-DNP IgE obtained as a monoclonal antibody from Miles Scientific, Naperville, Ill. The IgE stock as used contained up to 20% IgG contamination. The grids were lifted from this solution and placed at 4° C. in 150 mM NaCl, pH 7.4 for 3 days. The crystal domains that formed yielded arrays of long range ordered with distinct optical diffraction spots as shown by the electron micrographs.

The same procedure was repeated, except that the phospholipid coated grids were not removed from the original IgE antibody solution but were allowed to incubate therein for 3 days. It was found that IgE was densely bound onto the phospholipid surface. There was no ordering or optical diffraction spots as shown by an electron micrograph.

EXAMPLE 3

Coated grids were floated on an IgE solution (50 μg/ml, 75 mM NaCl and 15 mM Tris) for 2 hours. The grids were transferred to a much higher ionic strength buffer (300 mM NaCl, 25 mM Tris) for 12 hours to promote crystal growth. By optical diffraction, several discrete spots were obtained from the electron micrographs. By contrast when a single step procedure was used for this same antibody-lipid system no order was achieved. At 300 mM NaCl not enough binding took place to cause 2-D crystallization and at the lower salinity, higher binding was achieved but with little ordering as measured by optical diffraction. In this example, the higher salinity of the second step promoted the nucleation of 2-D crystals, but this salinity could not be effectively used in a single step procedure alone.

Although the above examples are directed to only a few of the very many variables which can be used in the practice of the method of the present invention, it should be understood that the present invention is directed to the use of a much broader variety of proteins, phospholipids, salts, and substrates as shown in the description preceding these examples. Salts which can be used are alkali metal salts such as sodium chloride, and potassium chloride and alkaline earth salts such as calcium chloride and magnesium chloride.

What I claim as new and desired to secure by Letters Patent of the United States is:

1. A non-homogeneous method for promoting nucleation and crystal growth of at least one macromolecular protein monolayer on a supported phospholipid film comprising
   (1) floating the supported phospholipid film in a buffered saline solution which has been injected with a drop of the macromolecular protein in a nonhomogeneous manner, and
   (2) allowing the injected macromolecular protein to diffuse toward the supported phospholipid film surface for a period of at least one hour.

2. A non-homogeneous method of promoting nucleation and crystal growth of at least one macromolecular protein monolayer on a supported phospholipid film comprising
   (1) floating the supported phospholipid film in a buffered saline solution of the protein at a concentration of 10-200 micrograms/ml until a monolayer of the protein is formed, and
   (2) removing the resulting supported phospholipid film and floating it in a solution of the same protein at a lower concentration.

3. A non-homogeneous method of promoting nucleation and crystal growth of at least one macromolecular protein monolayer on a supported phospholipid film comprising
   (1) floating the supported phospholipid film in a buffered saline solution of the protein at a concentration of 100-200 micrograms/ml until a monolayer of the protein is formed, and
   (2) removing the resulting supported phospholipid film and floating it in a solution of a different protein at a concentration of 10-100 micrograms/ml.

4. A non-homogeneous method of promoting nucleation and crystal growth of at least one macromolecular protein monolayer on a supported phospholipid film comprising removing the coated supported phospholipid film and floating it in a salt solution comprising an alkaline metal salt having a concentration of at least 10 mM.

5. A non-homogeneous method for promoting nucleation and crystal growth of at least one macromolecular protein monolayer on a supported phospholipid film comprising
   (1) floating the supported phospholipid film in a buffered saline solution which has been superimposed over a layer of the protein,
   (2) allowing the macromolecular protein to diffuse toward the supported phospholipid film surface for a period of at least one hour.

* * * * *